United States Patent
Stumpe et al.

(10) Patent No.: US 10,706,328 B2
(45) Date of Patent: Jul. 7, 2020

(54) FOCUS-WEIGHTED, MACHINE LEARNING DISEASE CLASSIFIER ERROR PREDICTION FOR MICROSCOPE SLIDE IMAGES

(71) Applicant: Google LLC, Mountain View, CA (US)

(72) Inventors: Martin Stumpe, Belmont, CA (US); Timo Kohlberger, Mountain View, CA (US)

(73) Assignee: Google LLC, Mountain View, CA (US)

(*) Notice: Subject to any disclaimer, the term of this patent is extended or adjusted under 35 U.S.C. 154(b) by 191 days.

(21) Appl. No.: 15/972,929

(22) Filed: May 7, 2018

(65) Prior Publication Data
US 2019/0340468 A1 Nov. 7, 2019

(51) Int. Cl.
| | |
|---|---|
| G06K 9/00 | (2006.01) |
| G06K 9/62 | (2006.01) |
| G16H 30/40 | (2018.01) |
| G06N 20/00 | (2019.01) |
| G06K 9/03 | (2006.01) |
| G06N 3/08 | (2006.01) |

(52) U.S. Cl.
CPC ....... *G06K 9/6262* (2013.01); *G06K 9/00134* (2013.01); *G06K 9/00147* (2013.01); *G06K 9/036* (2013.01); *G06N 3/08* (2013.01); *G06N 20/00* (2019.01); *G16H 30/40* (2018.01); *G06K 2209/05* (2013.01)

(58) Field of Classification Search
CPC ........... G06K 2209/05; G06K 9/00134; G06K 9/00147; G06K 9/036; G06K 9/6262; G06N 20/00; G06N 3/08; G06T 2207/10056; G06T 2207/20021; G06T 2207/20081; G06T 2207/20084; G06T 2207/30168; G06T 7/0002; G16H 30/40
See application file for complete search history.

(56) References Cited

U.S. PATENT DOCUMENTS

| | | | |
|---|---|---|---|
| 7,456,377 | B2 | 11/2008 | Zeineh et al. |
| 9,575,301 | B2 | 2/2017 | Loney et al. |

(Continued)

OTHER PUBLICATIONS

Pantanowtiz, L., "Digital Images and the Future of Digital Pathology", Journal of Pathology Informatics, vol. 1, Aug. 10, 2010, 4 pages.

(Continued)

*Primary Examiner* — Xin Jia
(74) *Attorney, Agent, or Firm* — McDonnell Boehnen Hulbert & Berghoff LLP

(57) ABSTRACT

A method is described for generating a prediction of a disease classification error for a magnified, digital microscope slide image of a tissue sample. The image is composed of a multitude of patches or tiles of pixel image data. An out-of-focus degree per patch is computed using a machine learning out-of-focus classifier. Data representing expected disease classifier error statistics of a machine learning disease classifier for a plurality of out-of-focus degrees is retrieved. A mapping of the expected disease classifier error statistics to each of the patches of the digital microscope slide image based on the computed out-of-focus degree per patch is computed, thereby generating a disease classifier error prediction for each of the patches. The disease classifier error predictions thus generated are aggregated over all of the patches.

16 Claims, 7 Drawing Sheets

(56) References Cited

U.S. PATENT DOCUMENTS

2015/0220838 A1* 8/2015 Martin .................. G06N 5/04
                                                706/12
2017/0193657 A1* 7/2017 Madabhushi ............ G06N 3/08
2018/0322660 A1* 11/2018 Smith .................. G06K 9/6267

OTHER PUBLICATIONS

Mukhopadhyay, S. et al., "Whole Slide Imaging Versus Microscopy for Primary Diagnosis in Surgical Pathology: A Multicenter Blinded Randomized Noninferiority Study of 1992 Cases (Pivotal Study)", Am J Surg Pathol. vol. 42, No. 1, Jan. 2018, pp. 39-52.

Janowczyk, A. et al., "Deep Learning for Digital Pathology Image Analysis: A Comprehensive Tutorial with Selected Use Cases", Journal of Pathology Informatics, Jul. 26, 2016, 18 pages.

Ghaznavi, Farzad et al., "Digital Imaging in Pathology: Whole-Slide Imaging and Beyond", Annual Review of Pathology: Mechanisms of Disease, vol. 8, 2013, pp. 331-359.

Liu, Y, et al. "Artificial Intelligence-Based Breast Cancer Nodal Metastasis Detection", Archives of Pathology & Laboratory Medicine, 2018, pp. 1-10.

Senaras, Caglar et al., "DeepFocus: Detection of Out-of-Focus Regions in Whole Slide Digital Images Using Deep Learning", PLOS One, Oct. 25, 2018, pp. 1-13.

Models [Internet]. Github; Available: https://github.com/tensorflow/models, retrieved from internet Dec. 12, 2018, 1 page.

Liu, Y. et al., "Detecting Cancer Metastases on Gigapixel Pathology Images" [Internet]. arXiv [cs.CV]. 2017. Available: http://arxiv.org/abs/1703.02442, pp. 1-13.

Yang, Samuel J. et al., "Assessing Microscope Image Focus Quality With Deep Learning", BMC Bioinformatics, vol. 19, 2018, pp. 1-9.

McGraw, Tim, "Fast Bokeh Effects Using Low-Rank Linear Filters", The Visual Computer, vol. 31, No. 5, May 2014, 20 pages.

Lopez, Xavier Moles et al., "An Automated Blur Detection Method for Histological Whole Slide Imaging", PLOS One, vol. 8, No. 12, Dec. 2013, pp. 1-11.

Campanella, Gabriele et al., "Towards Machine Learned Quality Control: A Benchmark for Sharpness Quantification in Digital Pathology", Computerized Medical Imaging and Graphics, 2017, https://doi.org/10.1016/j.compmedimag.2017.09.001, pp. 1-10.

Shakeri, S. Mojtaba et al., "Optical Quality Assessment of Whole Slide Imaging Systems for Digital Pathology", Optics Express, vol. 23, No. 2, Jan. 26, 2015, pp. 1319-1336.

Liao, Jun et al., "Rapid Focus Map Surveying for Whole Slide Imaging With Continues Sample Motion", Optics Letters, vol. 42, No. 17, 2017, pp. 3379-3382.

Kayser, Klaus et al., "How to Measure Image Quality in Tissue-Based Diagnostic (Diagnostic Surgical Pathology)", Diagnostic Pathology, 9th European Congress on Telepathology and 3rd International Congress on Virtual Microscopy, Toledo Spain, Diagnostic Pathology, vol. 3, Jul. 15, 2008, pp. 1-7.

Gurcan, Metin N. et al., "Histopathological Image Analysis: A Review", IEEE Rev, Biomed. Eng., vol. 2, 2009, doi:10.1109/RBME.2009.2034865, pp. 1-59.

Szegedy, C. et al., "Going Deeper with Convolutions", arXiv:1409.4842 [cs.CV], Sep. 17, 2014, pp. 1-12.

Szegedy, C. et al., "Rethinking the Inception Architecture for Computer Vision", arXiv:1512.00567 [cs.CV], Dec. 11, 2015, 10 pages.

Szegedy, C. et al., "Inception-v4, Inception-ResNet and the Impact of Residual Connections on Learning", Proceedings of the Thirty-First AAAI Conference on Artificial Intelligence, AAAI-17, vol. 4, 2017, pp. 4278-4284.

* cited by examiner

| OOF degree | mean error Case 1 | mean error Case 2 | ... |
|---|---|---|---|
| 0 (in-focus) | 0.15% | 0.35% | ... |
| 1 | 1.5% | 1.7% | ... |
| 2 | 2.5% | 2.1% | ... |
| ... | ... | ... | ... |

Fig. 4

Expected disease classifier error statistics for out of focus degrees — 220

| OOF degree | 40X magnification | 20X magnification | 10X magnification |
|---|---|---|---|
| 0 (in-focus) | 0.04% | 0.07% | 0.18% |
| 1 | 1.5% | 1.7% | 2.5% |
| 2 | 2.2% | 2.7% | 3.2% |
| 3 | 2.5% | 3.1% | 4.7% |
| ... | ... | ... | ... |

Expected disease classifier
error per image patch

FOCUS-WEIGHTED, MACHINE LEARNING DISEASE CLASSIFIER ERROR PREDICTION FOR MICROSCOPE SLIDE IMAGES

BACKGROUND

This disclosure relates to a method for generating a prediction of a disease classification (or equivalently, diagnosis) error generated by a machine learning classifier for a microscope slide image. The predicted error is weighted by the degree to which portions of the image are out-of-focus ("OOF").

In the medical field of histopathology, microscopic images of human tissue samples (which a prepared onto glass slides) are used for rendering cancer diagnosis. In classic histopathology, a tissue sample is diagnosed visually by an expert using a microscope. By contrast, in the newer sub-field of digital pathology, a high-resolution digital image of a sample is acquired by a whole-slide scanner first, and diagnosis is done in a subsequent step at a computer screen. Alternatively, the identification of cancerous cells in a tissue image can be aided by machine learning algorithms, typically embodied as deep convolutional neural networks, which are trained to find cancer cells in magnified tissue images. Such algorithms can generate so-called "heat map" images in which areas of the slide are shown in contrasting color, e.g., red, to indicate areas which are predicted to contain cancer cells.

Tissue images from whole-slide scanners are typically of gigapixel size (e.g. 100,000×100,000 pixels at 40× magnification). One of the main technical problems, however, is that regions of the digitized images can often be blurry and out-of-focus, rendering the respective image regions unusable for accurate diagnoses both by human pathologists as well as machine learning algorithms. Achieving accurate focus is particularly challenging for whole-slide scanners because (1) the depth of field is extremely thin due to the high objective power used to digitize the image, and (2) the tissue is often uneven and not in the same focus plane.

The depth of field is reciprocal to the magnification, accordingly the depth of field is only extremely thin at high magnifications. The depth of field, also denoted as "focus range", especially at high magnifications, is often close to or even smaller than the thickness of the tissue to be captured. Moreover, the tissue sample is usually not perfectly planar, but uneven, and its thickness varies often too. Therefore, slide scanners usually employ a local auto-focus method while capturing images in smaller stripes or tiles, which are then digitally stitched together to form a whole-slide image. None of the auto-focus solutions employed by the different scanner manufacturers are perfect, but rather can fail in some image regions to keep the majority of the tissue within the focus range, and thus cause out-of-focus blur of varying degrees.

The main challenge for the auto-focus algorithm thereby is to distinguish between (a) blurriness in in-focus image regions caused by tissue with smooth appearance and (b) blurriness of any tissue pattern caused by varying degrees of out-of-focus. A secondary challenge is to prevent focusing on foreign particles on top of the "cover slip" (plastic or glass slide covering the tissue sample), such as dust or debris, which usually results in the tissue to be far outside the focus range.

Literature relating to the problems of quantifying the degree of out-of-focus for tissue images and related topics includes the following: G. Campanella et al., *Towards machine learned quality control: A benchmark for sharpness quantification in digital pathology*. Computerized Medical Imaging and Graphics (2017) https://doi.org/10.1016/j.compmedimag.2017.09.001; K. Kayser et al., How to measure image quality in tissue-based diagnosis (diagnostic surgical pathology), from 9th European Congress on Telepathology and 3rd International Congress on Virtual Microscopy, Toledo Spain Diagnostic Pathology 2008 3 (suppl. 1); J. Liao et al., Rapid focus map surveying for whole-slide imaging with continues [sic] sample motion , arXiv: 1707.03039 [cs.CV] June 2017; S. Shakeri et al., *Optical quality assessment of whole-slide imaging systems for digital pathology* Optics Express Vol. 23, Issue 2, pp. 1319-1336 (2015); X. Lopex et al., *An Automated Blur Detection Method for Histological Whole-slide Imaging*, PLOS one (Dec. 13, 2013) https://doi.org/10.1371/journal.pone.0082710; Samuel Yang et al., "*Assessing microscope image focus quality with deep learning*", BMC Bioinformatics (2018) 19:77, and M. Gurcan et al. *Histopathological Image Analysis: A Review* IEEE Rev Biomed Eng. 2009; 2: 147-171.

The present inventors have appreciated that the degree to which a slide is out-of-focus can impact the accuracy of machine learning diagnosis or cancer cell identification, and that there is a need to quantifying the error in a machine learning disease classifier that is focus-weighted, i.e., the error is specifically attributable to the degree to which portions of the microscope slide image are out-of-focus. This disclosure addresses this need.

SUMMARY

In one aspect, a method for generating a prediction of a disease classification error for a magnified, digital microscope slide image of a tissue sample is disclosed. The method includes the steps of:

(a) scanning with a slide scanner a microscope slide containing the tissue sample and generating the digital microscope slide image, the digital microscope slide image composed of a multitude of patches of pixel image data;

(b) computing an out-of-focus degree per patch for the digital microscope slide image;

(c) retrieving data representing expected disease classifier error statistics of a machine learning disease classifier for a plurality of out-of-focus degrees;

(d) computing a mapping of the expected disease classifier error statistics to each of the patches of the digital microscope slide image based on the computed out-of-focus degree per patch computed in step (b) and the data retrieved in step (c) and thereby generating a disease classifier error prediction for each of the patches; and (e) aggregating the disease classifier error predictions generated in step (d) over all of the patches.

In another aspect, a pathology system is disclosed which includes, in combination, a) a slide scanner adapted to generate a digital slide image of a microscope slide;

b) a memory storing
  1) parameters for a deep convolutional neural network trained to compute an out-of-focus degree per patch for a digital microscope slide image generated by the slide scanner;
  2) data representing expected disease classifier error statistics of a machine learning disease classifier for a plurality of out-of-focus degrees; and c) a computer configured for computing (1) out-of-focus degree per patch for the digital microscope slide image using the deep convolutional neural network, (2) a mapping of the expected disease classifier error statistics to each of the patches of the digital microscope slide image based on the computed out-of-focus degree per patch and thereby generating a disease classifier error prediction for each of the patches; and (3) an aggregation of the disease classifier error predictions over all of the patches.

In one configuration, the microscope slide contains a prostate tissue sample. The machine learning disease classifier is trained to assign Gleason scores to portions of prostate tissue images. In another configuration, the tissue sample contains a lymph node sample obtained from a breast cancer patient. In this situation the machine learning disease classifier is trained to assign cancer/non-cancer labels to portions of the lymph node tissue images.

In one configuration, the memory and computer are local to the slide scanner. Alternatively, the memory and computer are remote to the slide scanner, for example in computing resources on a local area network connected to the slide scanner on in service provider computing resources in the cloud.

In another aspect, a method for generating a prediction of a disease classification error for a magnified, digital microscope slide image of a tissue sample is described. The digital microscope slide image is composed of a multitude of patches of pixel image data. The method includes the steps of:

(a) computing an out-of-focus degree per patch for the digital microscope slide image;

(b) retrieving data representing expected disease classifier error statistics of a machine learning disease classifier for a plurality of out-of-focus degrees;

(c) computing a mapping of the expected disease classifier error statistics to each of the patches of the digital microscope slide image based on the computed out-of-focus degree per patch computed in step (a) and thereby generating a disease classifier error prediction for each of the patches; and (d) aggregating the disease classifier error predictions generated in step (c) over all of the patches.

The computation of the out-of-focus degree per patch can be performed by a deep convolutional neural network trained to classify patches of tissue images by degree of out-of-focus.

In still another aspect, there is disclosed a method for characterizing a disease classifier configured to generate a classification label for digital microscope slide of a tissue sample or portion thereof. The method includes the steps of:

a) acquiring (e.g., receiving via an API call) a set of slide images ("master images" of FIG. 2), each composed of patches of pixel image data, which are in focus and which are associated with ground truth labels for each image patch;

b) defining a set of out-of-focus degrees, and for each degree:

1) applying a corresponding amount of synthetic out-of-focus to each of the patches of an image in the set of slides;

2) computing a disease classification error for each patch in the image; and 3) computing a mean error across all of the patches in the image;

c) storing the mean error computed in step b) 3) for all of the degrees defined in step b) as an expected error for the disease classifier for the out-of-focus degrees defined in step b); and d) repeating steps b1), b2), b3), and c) for each of the slide images in the set.

In one embodiment, the method may further include the step of repeating steps b), c) and d) at different magnifications for the slide images in the set. This results in generation of disease classifier error statistics for slide images at different magnifications. In one embodiment, the method can further comprise the step of repeating steps a), b), c) and d) at least once for each of a plurality of different slide scanners of different manufacturers. Different slide scanners of different manufacturers may produce images of different qualities and accordingly the disease classifier error statistics may vary from machine to machine. In this embodiment the disease classifier error statistics are obtained for each of set of different slide scanners so that the methodology of this disclosure may be generally used for a multitude of different machines from different manufacturers.

In one embodiment, the synthetic out-of-focus degrees which are applied to the master images are obtained using a computational Bokeh filter. Other methods for artificially blurring the master images could be used. Our experimentation indicates that computational or digital Bokeh filtering is a preferred method.

BRIEF DESCRIPTION OF THE DRAWINGS

FIG. 3 is an illustration of a computed mean disease classifier error, per patch, for different degrees of out-of-focus, for two of the master images.

FIG. 4 is an illustration of data representing the expected disease classifier error statistics for different out-of-focus degrees averaged over all of the reference images. The data shown in FIG. 4 is stored in memory and used to calculate the focus-weighted disease classifier error for a new slide as per the procedure of FIGS. 1 and 6.

DETAILED DESCRIPTION

Figure 1:
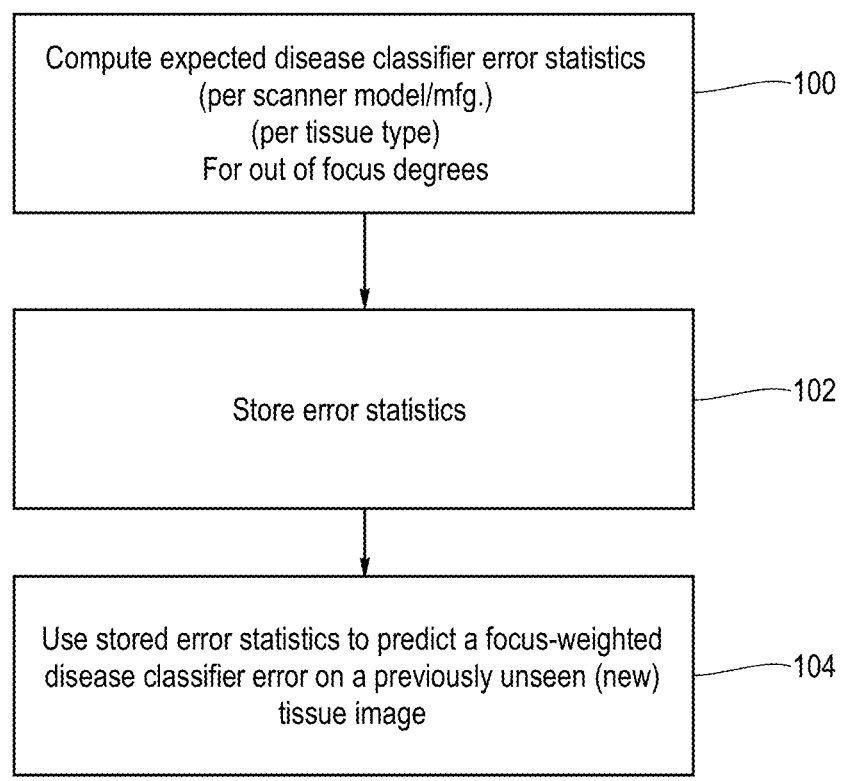
FIG. 1 is a flow chart showing a process of predicting a focus-weighted disease classifier error on a digital microscope image.

Digital pathology is advancing into clinical workflows, largely motivated by the potential of powerful image analysis tools using new machine learning techniques and enabled by the recent regulatory approval of the first Whole-Slide Image (WSI) scanner for primary diagnosis in the U.S., as well as wider availability of cloud storage and large IT infrastructure to handle gigapixel image files. However, the process of digitization adds sources for artifacts to the imaging process, including color or contrast problems and out-of-focus areas. These artifacts, and in particular out-of-focus areas, can negatively impact the suitability of the digital slide image for rendering an accurate diagnosis by a pathologist, or the accuracy of automated image analysis. A human pathologist will usually flag such an image as low quality and order a rescan, which causes potentially long delays with the case. Even worse, in automated image analysis, such image artifacts can directly translate into detection and classification errors. For instance, some studies found that systematic false positives can be traced back to bad focus quality, such as out-of-focus germinal centers being mistaken as tumor metastases by algorithms.

One option to mitigate these problems is to have a technician prescreen all digital slides that are produced by the scanner. This type of manual quality control, however, is impractical from a time and cost perspective, and even infeasible for exhaustive screening of small artifacts. The other option is to do automated quality control and evaluation of focus quality, which does not have any of the above limitations. While every WSI scanner has built-in focus evaluation that can be used for automatic rescans of the affected regions or for quality reporting, there are several shortcomings in the existing methods: (1) despite this built-in focus evaluation, the majority of slides scanned by a WSI scanner still have out-of-focus regions, (2) the focus evaluation methods across scanners are different, prohibiting comparison across devices, (3) the focus metrics can usually not be exported to the user in sufficient detail, such as a spatial distribution of focus quality, and (4) the evaluation does not take the clinical relevance of the focus quality into account. For instance, diagnoses that are based on cellular features, such as detection of breast cancer metastases, usually require even higher focus quality than diagnoses that are based primarily on the larger tissue morphology, such as prostate adenocarcinoma Gleason grading.

This document introduces a focus quality evaluation that address all of these shortcomings—it provides a generally applicable metric that is highly concordant with manually evaluated focus quality, can be applied to any WSI regardless of the scanning device, and provides spatial information of focus quality across the WSI. Moreover, we investigate the focus sensitivity of two diagnostic models for tumor detection and introduce a quality metric that takes the impact on focus quality for the particular clinical diagnosis task at hand into account to provide a relevance-weighted quality score for a slide image.

The methodology is shown in FIG. 1 at a high level. The method makes use a deep convolutional neural network which is trained to identify disease or tumor cells in digital microscope images ("disease classifier" herein). This deep convolutional neural network, or machine learning model, is not shown in FIG. 1, but can be configured as described in PCT application entitled "Method and System for Assisting Pathologist Identification of Tumor Cells in Magnified Tissue Images", serial no. PCT/US17/019051, filed Feb. 23, 2017. Deep convolutional neural network pattern recognizers are widely known in the art of pattern recognition and machine vision, and therefore a detailed description thereof is omitted for the sake of brevity. The Google Inception-v3 deep convolutional neural network architecture, which is a suitable architecture, is described in the scientific literature. See the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv:1512.00567 [cs.CV] (December 2015); see also U.S. patent application of C. Szegedy et al., "Processing Images Using Deep Neural Networks", Ser. No. 14/839,452 filed Aug. 28, 2015. A fourth generation, known as Inception-v4 is considered an alternative architecture. See C. Szegedy et al., Inception-v4, Inception-ResNet and the Impact of Residual Connections on Learning, arXiv:1602.0761 [cs.CV] (February 2016). See also U.S. patent application of C. Vanhoucke, "Image Classification Neural Networks", Ser. No. 15/395,530 filed Dec. 30, 2016. The description of the convolutional neural networks in these papers and patent applications is incorporated by reference herein.

Figure 2:
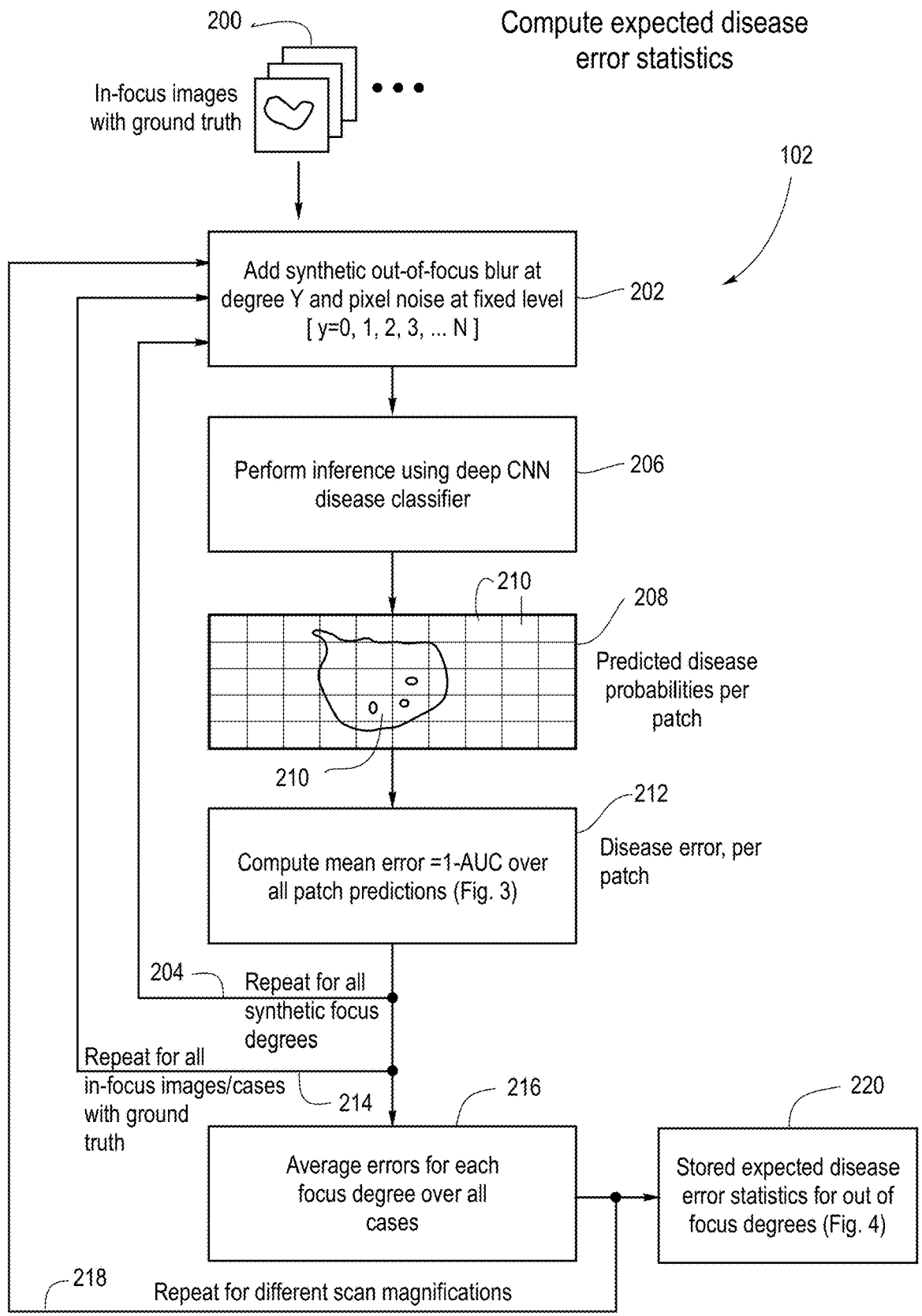
FIG. 2 is a flow chart showing a process for generating and computing expected disease classifier error statistics for use in the method of FIG. 1. The flow chart is executed on a set of in-focus, ground truth annotated images ("master images" herein) obtained from a particular whole-slide scanner of a particular manufacturer. The images consist of a multitude of patches of pixel image data. The process may be repeated several times in order to generate expected disease classifier error statistics for different whole-slide scanners of different manufacturers or different makes and models, as the expected disease classifier error statistics may vary between different makes and models of slide scanners.

Essentially, in the method of FIG. 1, in step 100 the expected disease classifier error statistics for the disease classifier neural network described in the previous paragraph are obtained for varying degrees of out-of-focus. The manner of obtaining these statistics from a large set of master images in the form of in-focus, ground truth annotated images, and artificially blurred to the different degrees of out-of-focus, is shown in FIG. 2 and will be described in detail below. An alternative method is to use partially out-of-focus scans as master images, by running the OOF classifier (described below) to determine patches that are in-focus and run the remainder of the "calibration algorithm" of FIG. 2 on those image patches. Once these statistics are obtained, by either method, they are stored, as indicated at 102, and then used later as indicated at step 104. In some sense, step 100 could be considered a quasi-calibration step. Essentially, we take measurements from the distribution P(e|OOF) with e being the disease classifier error for a single patch, and OOF the out-of-focus degree of the patch. In addition, we assume P( ) to be Gaussian distributions (by computing the mean and standard deviation across the per-OOF degree error measurements). We then assume these distributions to be the same for unseen image patches, and in step 104 predict the classifier errors to be the expected values of the per-OOF-degree Gaussians, which are the means. So, one could say that at step 100 we calibrate the disease error means and standard deviations to the OOF-degree levels.

At step 104 we use the stored error statistics (step 102) to predict a focus-weighted disease classifier error on a previously unseen, i.e., a "new" tissue image. Step 104 is performed at the time of use, that is, when a new tissue image is captured by a whole-slide scanner and the user wishes to understand the disease classifier error before assigning a diagnosis or label to the image or portion thereof. Step 104 makes use of a second deep convolutional neural network ("OOF Classifier") which is trained to identify the degree to which patches in the new image are out-of-focus. The architecture for the OOF Classifier may also be as described previously. In one possible configuration it may be configured and trained as described in Samuel Yang et al.: "Assessing microscope image focus quality with deep learning", BMC Bioinformatics (2018) 19:77. Step 104 is shown in greater detail in FIG. 6. One significant difference between our approach (similar to Yang et al.) and those of Campanella et al. cited previously in the Background is that the latter don't apply synthetic noise after the synthetic blurring (in order to simulate the original image sensor pixel noise which is removed almost completely by the synthetic blurring.). In our experiments we found the synthetic noise to be important to train a proper OOF classifier from synthetic training data. Without it, we found our classifier to fail to detect especially strong real OOF, where the noise is quite visible.

FIG. 2 is a flow chart showing the step 100 of FIG. 1 in greater detail. The procedure shown in FIG. 2 is to compute the expected disease error statistics for the disease classifier. As indicated at 200, we obtain a multitude (e.g., 100 or so, possibly more, and optionally at different magnification levels) of completely in-focus, ground truth annotated digital microscope slide images of a given tissue type, e.g., lymph nodes from breast cancer patients or prostate tissue. These images 200 are referred to as the "master images" in this document. The ground truth labels exist for each image patch, i.e., (i) cancer/non-cancer for lymph node breast metastasis, or (ii) Gleason score for a prostate tissue. These gigapixel images consists of a multitude of rectangular pixel patches or tiles, the patches are shown at 210 in block 208. The patch annotations can be performed manually by a trained pathologist or a team of pathologists. The size of the patches can vary depending on the tissue type and the particular disease classifier that is used. In a situation where a team of pathologists are used to assign ground truth (patch annotations), ground truth is determined from multiple annotations of the same patch. The following methods can be used if there is not unanimity: (a) majority vote, (b) force pathologists/annotators to adjudicate each patch where disagreeing votes are higher than a threshold or greater than zero; (c) apply (a) and for patches where there's no majority vote (e.g. for multi-class labels like Gleason) then do (b).

At step 202, we add a synthetic (artificial) out-of-focus blur to the images 200 with the pixel noise level fixed, both at varying degrees. The blur is added at different degrees or amounts of blur, indicated by parameter Y, where Y can take integer values from 0 (no blur) to N, where N can be 4, 10, or some other number such as 29. By contrast, the synthetic noise (multiplicative Poisson noise to be precise) degree does not depend on Y, but is randomly chosen from a range, which was determined prior from measuring noise levels of (non-blurred) original images. As indicated by loop 204 we repeat the process of creating synthetic OOF blur, and perform steps 206 and 212 for all values of Y. The OOF blur is preferably performed using a computational Bokeh filter, the details of which are explained in the paper of Tim McGraw, *Fast Bokeh Effects Using Low-Rank Linear Filters*, The Visual Computer vol. 31 no. 5 (May 2014), the content of which is incorporated by reference herein. The Summed Area Tables approach described at page 3 of the McGraw paper is a suitable approach for the instant application.

Then, for each degree of out-of-focus (Y=0 ... N), steps 206 and 212 are performed. At step 206, we perform inference using the Disease Classifier and assign a label (e.g., cancer/no cancer, or Gleason score) to each of the patches in one of the images at that degree of OOF. The result of step 206 can be represented as a "heat map" showing the predicted disease probabilities for each patch in the entire slide 200. This heat map is shown at 208 with the patches 210 not shown to scale. The small circles in the tissue blob for example could be red to indicate high probability of containing cancer cells.

At step 212, we first use the predictions generated at step 206 and the ground truth annotations for each patch to compute the disease classifier error for each patch. Then, we aggregate these results to compute a mean error=1−AUC over all patch predictions for this specific out of focus degree Y. We then store this result as the expected error for this synthetic blur level and this particular disease classifier. Note: the 1−AUC error metric applies for 2-class disease classifiers. For multi-class classifiers other metrics apply. Such metrics are described in further detail below.

As indicated by step 214 we repeat the loop 204 for each of the in-focus images with ground truth 200.

By repeating steps 206, and 212 for each degree of OOF we end up with a table shown as FIG. 3. For each OOF degree (0, 1, 2 ... ) we have the mean error computed in step 212 for each of the master images 200 (identified as case 1, case 2 ... ).

Then at step 216 we the average the errors for each OOF degree over all cases/master images. As indicated at loop 218, we repeat this process for different scan magnifications, thereby obtaining expected disease error statistics for all of the images at different magnifications. The different magnifications can be obtained from upsampling or downsampling the images 200 or by obtaining physical tissue slides instead of the images 200 and scanning them at different magnifications. The results are then stored in a table 220 shown in FIG. 4. FIG. 4 shows the expected disease classifier error statistics for different out-of-focus degrees at different magnification levels.

It will be appreciated that the procedure of FIG. 2 can be performed many times for different types of master images 200 and disease classifiers, such as once for the lymph node master set of in-focus images and a lymph node metastasis classifier and once for a prostate tissue master set of in-focus images and a prostate Gleason scoring classifier. Additionally, the procedure of FIG. 2 can be performed repeatedly to generate disease classifier error statistics for different makes and models of whole-slide scanners. For example, the procedure for FIG. 2 could be performed once to generate disease classifier error statistics for a Hamamatsu whole-slide scanner and then a second time for an Aperio line scan whole-slide scanner, or other makes and models that are currently in use commercially. This is because the disease classifier error statistics may vary from scanner to scanner, as the scanners perform differently in terms of image and focus quality.

Figure 5:
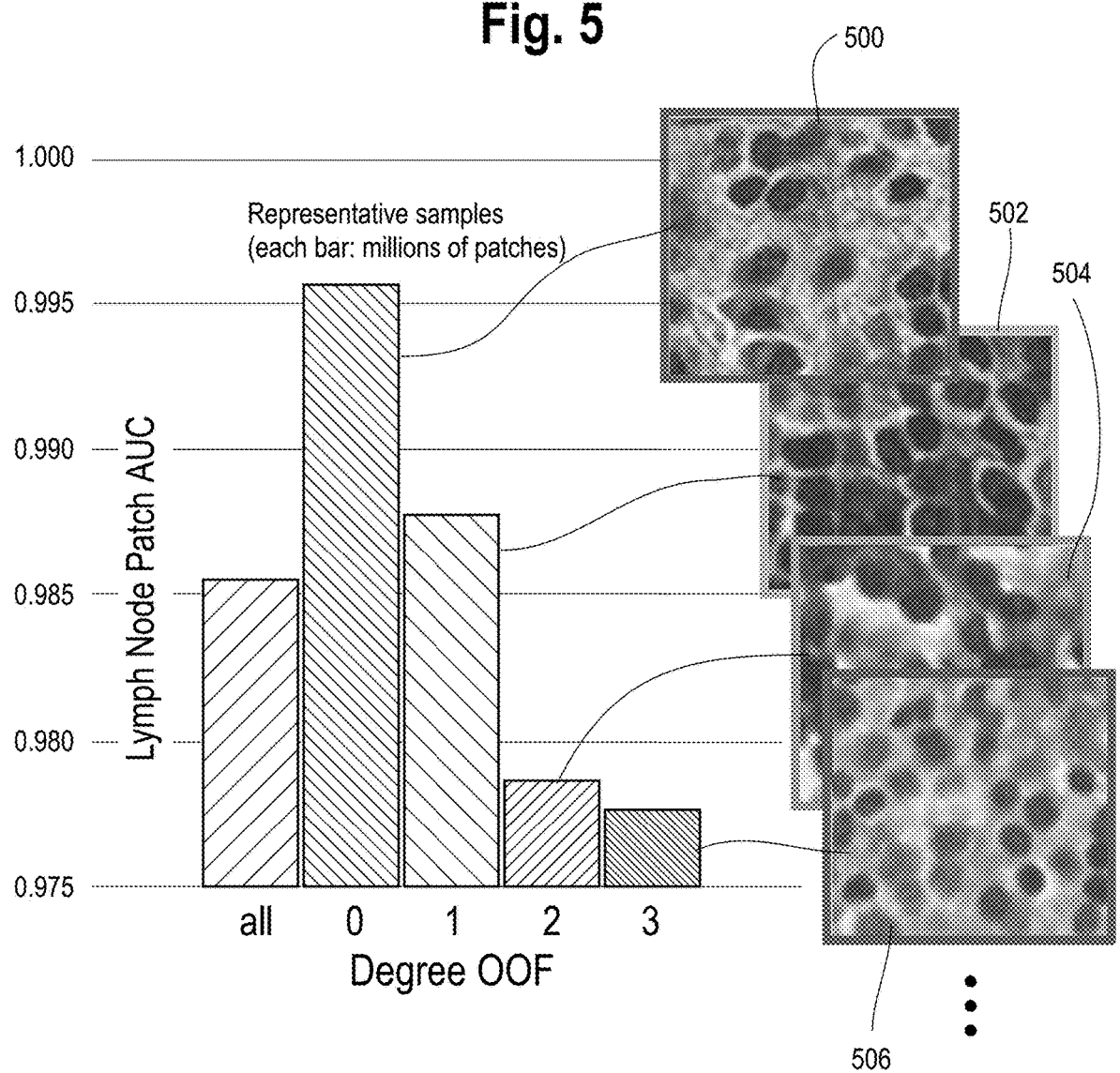
FIG. 5 is an illustration of the disease classifier error for degrees of out-of-focus for all the master images.

FIG. 5 shows an example of the result of FIG. 2, in terms of a plot of the disease classifier performance (AUC) for a particular disease classifier (in this example lymph node metastasis classification on a patch of pixels) at a given magnification power. The X axis indicates the degree of out-of-focus (0 being completely in focus) and examples of the images 500, 502, 504 and 506 at each degree of out-of-focus. In FIG. 5, only OOF degrees up to "3" are shown but AUC performance could be plotted for further OOF degrees (not shown in FIG. 5). It will be seen from FIG. 5, as expected, that the disease classifier has the highest classification accuracy for OOF degree 0 (completely in focus) and the classification accuracy drops significantly for OOF degrees 1 and 2, and less so for OOF degree 3. It will also be appreciated from FIG. 4 that while the disease error statistics indicate the disease classifier has higher performance at 40× as compared to 20× and 10× magnification, this may not necessarily be the case for all types of disease classifiers, and it may be that for some disease classifiers the classifier performance is actually higher at lower magnification (10×) than it is at higher magnifications, for example when larger scale structures and tissue morphology are significant in generating disease classifications which are most readily apprehended at lower power.

Once the disease classifier error statistics are obtained and stored as per the procedure of FIG. 2, they can be used at the time of use on a new (previously unseen) digital magnified tissue image in order to generate a disease classifier error prediction for all or part of the image. This procedure is shown at 104 in FIG. 1 and in more detail in FIG. 6. The "new" tissue image is shown at 600. At step 602 we perform inference on the image 600 using the OOF classifier described previously. This classifier is trained to generate a prediction of the degree to which each of the patches in the image 600 is out-of-focus, using the out-of-focus degree scale which was used in FIG. 2, in this example Y=0 . . . 29 where 0 is completely in focus and 29 is completely out-of-focus. The results of the inference step 206 can be represented as a heat map of the image 600 such as shown at 604, where the more out-of-focus patches in the image are colored light and the more in focus areas are given a darker color in accordance with the scale to the right of the heat map 604.

Then in step 606 for each patch we map the focus degree to the expected disease classifier error using the error statistics computed from FIG. 2 (see FIG. 4). This mapping can be conceptualized as a second heap map shown in FIG. 7, where the OOF degrees from heat map 604 (FIG. 6) are translated or mapped to disease classifier error as indicated at 606 in FIG. 6. Note that the patches of the heat map 604 in FIG. 6 which are the most out-of-focus have the highest expected disease classifier error (the higher degrees of classifier error are also light color in FIG. 7 whereas the areas with the least classifier error are shown darker in FIG. 7.) Accordingly, this mapping is simply assigning a disease classifier error to a patch based on the patch's OOF degree using the stored error statistics and repeating this algorithm for all patches.

Then at step 608 we aggregate the predictions of the patch errors (illustrated in FIG. 7) to the whole-slide image. In one embodiment this aggregation can take the form of a computation of a disease classifier error score for the whole-slide. There are several possible methods by which this aggregation can be computed. One method is as follows:

a. Apply a disease/tissue type-specific threshold to the predicted classifier error prediction for each patch, e.g. 1.3%, essentially creating a binary mask of those patches with the predicted error above or below the threshold.

b. Apply Connected Component Analysis to the binary mask of a.

c. Drop every "connected components" region with an area smaller than a disease/tissue type-specific minimum area A, e.g. 200 sq. microns.

d. Sum up areas of remaining regions to gain the final metric, in this example an area metric indicating how much of the slide has the disease classifier error below the threshold and excluding the areas that are too small as per c. This metric could be presented as as absolute area metric, or as a percent metric, e.g., percent of the tissue area in the image which has the disease classifier metric below the threshold.

Another simple way of aggregating the predictions of patch errors to the whole slide would be to just count pixels above/below a error threshold without any connected component analysis and report the result as a percent of the tissue portion of the image.

At step 608, we then report a focus-weighted disease classifier error prediction for the whole-slide. For example, on a computer workstation used by a pathologist which is reviewing the image 600 of FIG. 6, the error prediction could be reported in a pop-up window on the display of the workstation alongside the image. Alternatively, the disease classifier error prediction could be reported in a screen used by the pathologist to enter a finding or diagnosis associated with the tissue image.

The above example has been in the context of a lymph node metastasis detector which predicts probability of breast cancer metastasis in a lymph node tissue image, and such as classifier would normally operate at 40× or 20× magnification, generate a class label of cancer/non-cancer for each of the patches in the image, and use as an error metric 1.0–AUC, where AUC is the receiver operating characteristic plot for the classifier's performance. Such an error metric is shown in FIGS. 3 and 4. For a prostate cancer classifier, this classifier predicts a Gleason score on each patch of pixels in a prostate tissue image and typically operates at 10× magnification. The class labels assigned by the classifier on each patch is in the set {none, 1, 2, 3, 4, 5 and 6} where 1 . . . 6 are Gleason scores known in the art. The error metrics for such as classifier may take a different format, such as weighted Cohen's Kappa (κ), a known statistical metric, or an average over one versus other classes AUCs.

Figure 6:
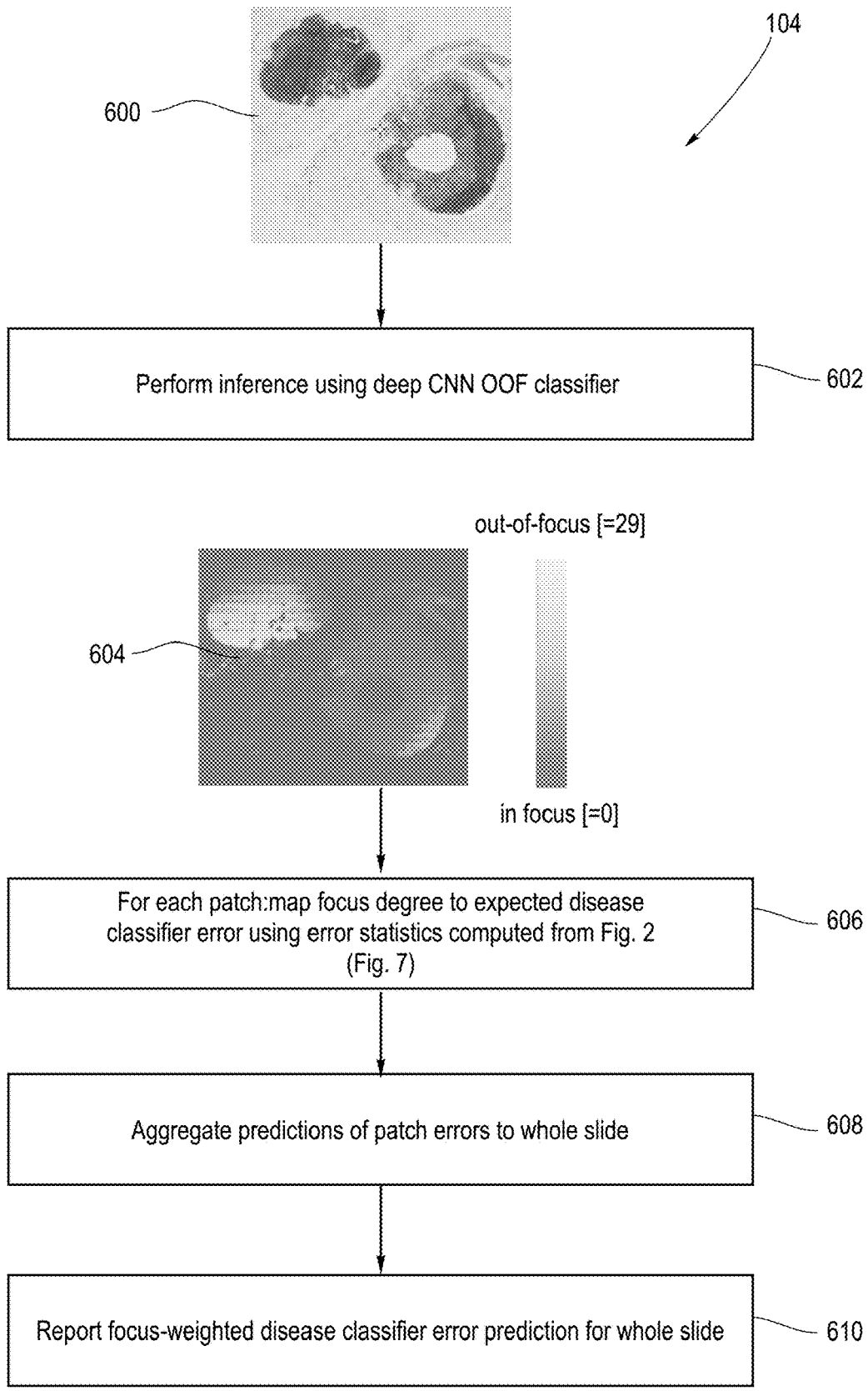
FIG. 6 is a more detailed illustration of a procedure for predicting a focus-weighted disease classifier error for a new slide as per FIG. 1, using the stored error statistics of FIG. 4 and generated in accordance with FIG. 2.

The computations shown in FIG. 6 could be implemented locally in computing resources of a whole-slide scanner such that the scanner both scans the slide and then generates the disease classifier error statistics and reports them both to a connected pathology workstation. In this embodiment, the scanner includes a processing unit and the deep CNN focus classifier as well as a data store storing the statistics of FIG. 4, as well as software for implementing the procedure explained in FIG. 6.

Figure 7:
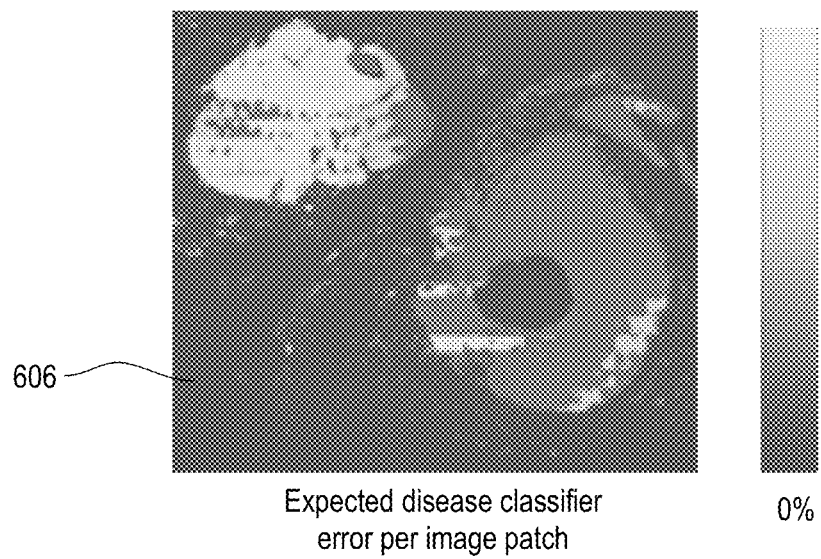
FIG. 7 is an illustration of the expected disease classifier error per image patch calculated in accordance with FIG. 6.
Figure 8:
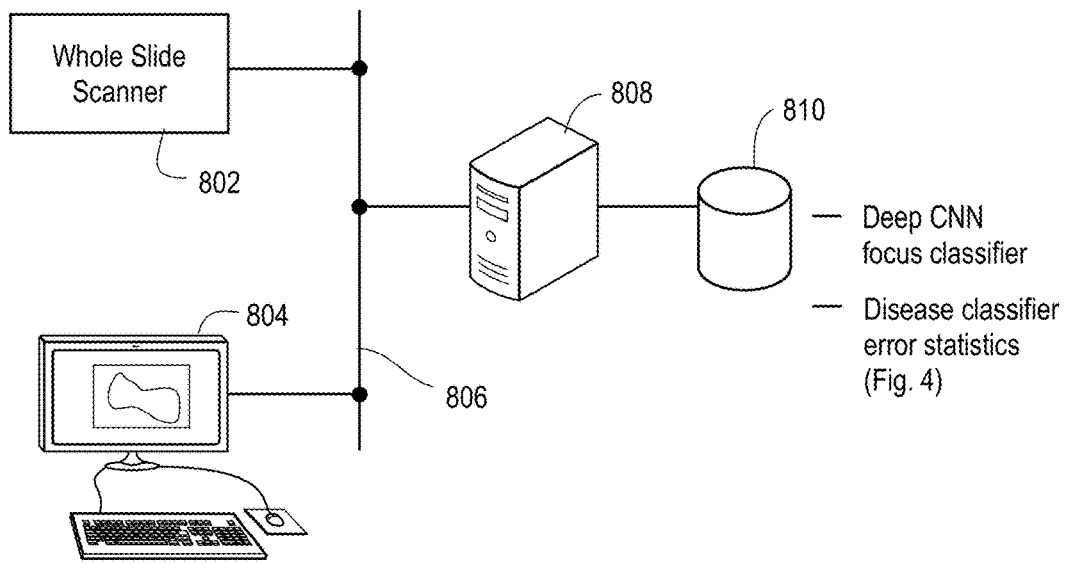
FIG. 8 is an illustration of one application of the method of FIG. 1 to a computing environment featuring a whole-slide scanner and a networked pathology workstation.

Several other alternative configurations are possible, one of which is shown in FIG. 8. In this implementation, the whole-slide scanner 802 is connected to a local area network 806 to which a pathology workstation 804 is also connected. This network 806 could for example take the form of a network in a hospital or medical clinic equipped with both the scanner and the pathology workstation. The network also has a computing resource 808, which could also take the form of a general purpose computer, which is connected to a data store or memory storing the parameters for the deep CNN focus classifier and disease classifier error statistics of FIG. 4, as well as code for implementing the procedure of FIG. 6. In use, when the scanner 802 scans the slide (not shown) and generates the image 600 of FIG. 6, the image is passed to the computing resource 808 which then implements the procedure of FIG. 6 and forwards the disease classifier error metrics to the workstation 804. The reporting of the disease classifier error prediction (step 610 of FIG. 6) could take the form of a heat map such as shown in FIG. 7 along with the aggregated prediction of patch errors computed at step 608.

Figure 9:
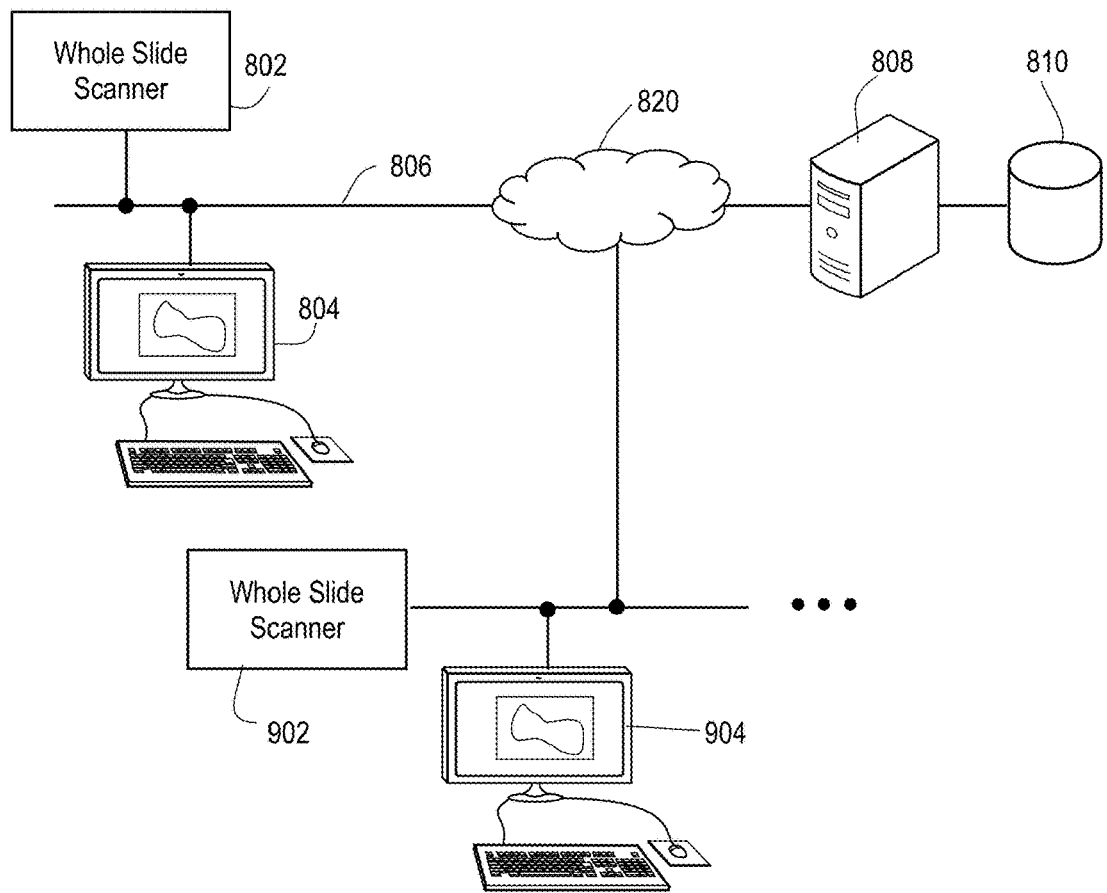
FIG. 9 is an illustration of a second application of the method of FIG. 1 to a computing environment featuring a whole-slide scanner and a networked pathology workstation, in which the generation of the focus-weighted disease classifier error occurs in computing systems in a remote network, and the results are transmitted to the pathology workstation.

FIG. 9 is another example of a system implementing the methods of this disclosure. In this example, the whole-slide scanner 802 and workstation 804 are on a network 806 which is connected to the cloud 820 (internet). A service provider in the cloud 820 operates a computing resource 808 with connected data store 810. The service provider receives images (600, FIG. 6) from the scanner 802 and by virtue of storing the deep CNN focus classifier and the disease classifier error statistics in the data store 810 and generates the disease classifier error predictions for the image and reports them back to the pathology workstation 804. The transmission of the image 600 (FIG. 6) to the service provider is accompanied by metadata for the image indicating the magnification level and make/model of the whole-slide scanner so that the proper disease classifier error statistics can be retrieved and used as appropriate for the particular image. The service provider performs this service for a multitude of distributed pathology laboratories, hospitals, clinics, universities, etc., one of which is indicated by the separate whole-slide scanner and pathology workstation 904 also connected to the cloud 820.

Further Considerations

The number of OOF degrees in the scale used in FIG. 2 loop 204 can vary and it is also possible to use a floating point scale.

The aggregation of prediction of patch errors for the new image in FIG. 6, step 608 could take other forms such as a) the absolute tissue area and percentage of total tissue area where predicted error above a classifier-dependent threshold, or b) total area of distinct tissue regions that are individually larger than a disease-specific size and for which the predicted errors are larger (or smaller) than a disease-specific predicted threshold, or c) a mean expected error (i.e., the average across all tissue patches, or min/max error statistics, or still some other format.

The main use of the aggregated error metrics are to report them alongside slide-level predictions, such as the slide-level Gleason score. E.g. an automated system could report to clinician/pathologist a Gleason score 4+3, but with a focus-dependent predicted error of 3%. The predicted error then could trigger (a) an additional microscope-based manual examination by a pathologist, or (b) or it could trigger a re-scan of the slide, if the error is particularly high. Moreover, in scenario (a) the pathologist could use the heatmap to prioritize regions with high error predictions when doing the additional manual microscope examination.

From the foregoing, it will be appreciated that we have described a pathology system comprising, in combination a) a slide scanner (FIG. 8, 802) adapted to generate a digital slide image of a microscope slide; b) a memory (FIG. 8, 810) storing
  1) parameters for a deep convolutional neural network trained to compute an out-of-focus degree per patch for a digital microscope slide image generated by the slide scanner;
  2) data representing expected disease classifier error statistics of a machine learning disease classifier for a plurality of out-of-focus degrees; and c) a computer (FIG. 8, 808) configured for computing (1) out-of-focus degree per patch for the digital microscope slide image using the deep convolutional neural network (FIG. 6, 602), (2) a mapping of the expected disease classifier error statistics to each of the patches of the digital microscope slide image based on the computed out-of-focus degree per patch and thereby generating a disease classifier error prediction for each of the patches (FIGS. 6, 606); and (3) an aggregation of the disease classifier error predictions over all of the patches (FIG. 6, 608).

It will also be appreciated that we have described a method for generating a prediction of a disease classification error for a magnified, digital microscope slide image of a tissue sample (FIG. 6, 600), the digital microscope slide image composed of a multitude of patches of pixel image data. The method includes the steps comprising the steps of:
  (a) computing an out-of-focus degree per patch for the digital microscope slide image; (FIG. 6, 602)
  (b) retrieving data representing expected disease classifier error statistics of a machine learning disease classifier for a plurality of out-of-focus degrees; (FIG. 2, 220)
  (c) computing a mapping of the expected disease classifier error statistics to each of the patches of the digital microscope slide image based on the computed out-of-focus degree per patch computed in step (a) and thereby generating a disease classifier error prediction for each of the patches; and (FIG. 6, 606)
  (d) aggregating the disease classifier error predictions generated in step (c) over all of the patches. (FIG. 6, 608).

It will also be appreciated that we have described a method for characterizing a disease classifier configured to generate a classification label for digital microscope slide of a tissue sample or portion thereof, see generally FIG. 2 and the description thereof above. The method includes a step of acquiring a set of slide images (FIG. 2, 200) (e.g., via an application programming interface (API) call to a data store storing such images, or from physically scanning a set of tissue slides with a whole slide scanner), each composed of patches of pixel image data, which are in focus and which are associated with ground truth labels for each image patch;
  b) defining a set of out-of-focus degrees (e.g., degrees of-of-focus Y on a scale of 0 (in focus to N where N is some integer in a range 1, 2, 3 . . . N), and for each degree:
    1) applying a corresponding amount of synthetic out-of-focus to each of the patches of an image in the set of slides; (FIG. 2, 202)
    2) computing a disease classification error for each patch in the image; (FIG. 2, 206)
    3) computing a mean error across all of the patches in the image; (FIG. 2, 212)
  c) storing the mean error computed in step b) 3) for all of the degrees defined in step
  b) as an expected error for the disease classifier for the out-of-focus degrees defined in step b); (FIG. 2, loop 204 for all synthetic out of focus degress)
  d) repeating steps b1), b2), b3), and c) for each of the slide images in the set. (loop FIG. 2, loop 214)

In the above method, steps a), b), c) and d) can be repeated at least once for each of a plurality of different slide scanners of different manufacturers.

In one embodiment the tissue sample is in the form of a prostate tissue sample. Alternatively, the tissue sample can be a lymph node sample. The synthetic out-of-focus applied at step b) 1) is applied using a computational Bokeh filter in a preferred embodiment. The expected error in one embodiment can be represented by 1.0 minus the area under a receiver operating characteristic curve (AUC) for the disease classifier. As shown in FIG. 3 and in FIG. 4 mean error stored in step c) is stored in a table format of degrees of out-of-focus and associated expected disease classifier errors.

We claim:

1. A method for generating a prediction of a disease classification error for a magnified, digital microscope slide image of a tissue sample, comprising the steps of:
  (a) scanning with a slide scanner a microscope slide containing the tissue sample and generating the digital microscope slide image, the digital microscope slide image composed of a multitude of patches of pixel image data;
  (b) computing an out-of-focus degree per patch for the digital microscope slide image;
  (c) retrieving data representing expected disease classifier error statistics of a machine learning disease classifier for a plurality of out-of-focus degrees;
  (d) computing a mapping of the expected disease classifier error statistics to each of the patches of the digital microscope slide image based on the computed out-of-focus degree per patch computed in step (b) and thereby generating a disease classifier error prediction for each of the patches; and (e) aggregating the disease classifier error predictions generated in step (d) over all of the patches.

2. The method of claim 1, wherein the tissue sample comprises a prostate tissue sample.

3. The method of claim 1, wherein the tissue sample comprises a lymph node sample.

4. The method of claim 1, wherein step b) is performed by a deep convolutional neural network trained to classify patches of tissue images by degree of out-of-focus.

5. The method of claim 1, further comprising step (f): generating a focus-weighted disease classifier error prediction for the digital microscope slide image as a whole.

6. The method of claim 1, wherein steps b) e) are performed locally by computing resources in the slide scanner.

7. A method for generating a prediction of a disease classification error for a magnified, digital microscope slide image of a tissue sample, the digital microscope slide image composed of a multitude of patches of pixel image data, comprising the steps of:
(a) computing an out-of-focus degree per patch for the digital microscope slide image;
(b) retrieving data representing expected disease classifier error statistics of a machine learning disease classifier for a plurality of out-of-focus degrees;
(c) computing a mapping of the expected disease classifier error statistics to each of the patches of the digital microscope slide image based on the computed out-of-focus degree per patch computed in step (a) and thereby generating a disease classifier error prediction for each of the patches; and
(d) aggregating the disease classifier error predictions generated in step (c) over all of the patches.

8. The method of claim 7, wherein the tissue sample comprises a prostate tissue sample.

9. The method of claim 7, wherein the tissue sample comprises a lymph node sample.

10. The method of claim 7, wherein step (a) is performed by a deep convolutional neural network trained to classify patches of tissue images by degree of out-of-focus.

11. The method of claim 8, further comprising step (e): generating a focus-weighted disease classifier error prediction for the digital microscope slide image as a whole.

12. A system for generating a prediction of a disease classification error for a magnified, digital microscope slide image of a tissue sample obtained by a microscope slide scanner, the digital microscope slide image composed of a multitude of patches of pixel image data, comprising:
(a) a computer memory storing non-transient data representing expected disease classifier error statistics of a machine learning disease classifier for a plurality of out-of-focus degrees; and
(b) a programmed computer configured with instructions for computing (1) an out-of-focus degree per patch for the digital microscope slide image and (2) a mapping of the expected disease classifier error statistics to each of the patches of the digital microscope slide image based on the computed out-of-focus degree per patch computed in (1) and thereby generating a disease classifier error prediction for each of the patches, the programmed computer further configured with instructions (3) for aggregating the disease classifier error predictions for each of the patches over all of the patches.

13. The system of claim 12, wherein the tissue sample comprises a prostate tissue sample.

14. The system of claim 12, wherein the tissue sample comprises a lymph node sample.

15. The system of claim 12, wherein the programmed computer is configured with instruction (4) for generating a focus-weighted disease classifier error prediction for the digital microscope slide image as a whole.

16. The system of claim 12, further comprising a slide scanner creating the digital microscope slide image and wherein the programmed computer comprises computing resources incorporated in the slide scanner.

* * * * *